United States Patent
Sumanaweera et al.

(10) Patent No.: US 6,659,953 B1
(45) Date of Patent: Dec. 9, 2003

(54) MORPHING DIAGNOSTIC ULTRASOUND IMAGES FOR PERFUSION ASSESSMENT

(75) Inventors: Thilaka S. Sumanaweera, Los Altos, CA (US); Robert W. Steins, Santa Clara, CA (US)

(73) Assignee: Acuson Corporation, Mountain View, CA (US)

(*) Notice: Subject to any disclaimer, the term of this patent is extended or adjusted under 35 U.S.C. 154(b) by 0 days.

(21) Appl. No.: 10/251,044

(22) Filed: Sep. 20, 2002

(51) Int. Cl.[7] .................................................. A61B 8/00
(52) U.S. Cl. .................................... 600/443; 600/441
(58) Field of Search ................................. 600/440, 443, 600/441, 455, 456, 437

(56) References Cited

U.S. PATENT DOCUMENTS

| 5,503,153 A | 4/1996 | Liu et al. |
| 6,015,384 A | * 1/2000 | Ramamurthy et al. ...... 600/440 |
| 6,162,174 A | 12/2000 | Friemel |
| 6,236,872 B1 | * 5/2001 | Diab et al. .................. 600/323 |

* cited by examiner

Primary Examiner—Marvin M. Lateef
Assistant Examiner—Maulin Patel

(57) ABSTRACT

An ultrasound image is morphed for perfusion assessment. Various images within a sequence of images or movie clip are mapped to one frame of reference using local warping. Nonlinear local image transformations or other warping based on local estimates of motion are used to interpolate different images to the common reference. The elastic stretching and compression of local image data results in a sequence of images where the same spatial location in each image represents the substantially same spatial location of the imaged tissue. The organ, tissue or region of interest is stationary throughout the sequence of images.

22 Claims, 5 Drawing Sheets

MORPHING DIAGNOSTIC ULTRASOUND IMAGES FOR PERFUSION ASSESSMENT

BACKGROUND

The present invention relates to morphing diagnostic ultrasound images. In particular, diagnostic ultrasound images are transformed for enhancing perfusion assessment. To measure perfusion in an organ, such as the liver or kidney, with ultrasound, added contrast agents or microspheres are injected into a patient. Ultrasound is then used to image the contrast agents as the contrast agents perfuse throughout the organ or tissue of interest. Any of various techniques may be used to detect the contrast agents, such as a loss of correlation between sequential pulses caused by movement or destruction of the contrast agent or B-mode detection. The wash-in or wash-out of contrast agent from the tissue of interest is analyzed to determine a rate or amount of perfusion. The intensity of the detected contrast agent is plotted as a function of time as a curve representing the wash-in or wash-out of the contrast agent.

The time-intensity curve may be inaccurate due to movement. The tissue of interest may move relative to the transducer due to breathing, the effects of the cardiac cycle, unintentional movement of the transducer by the user, or other sources of movement. As a result, the imaged tissue appears to move around within a sequence of ultrasound images. Parameterizing or calculating a time-intensity curve is difficult or inaccurate since a given spatial location in an image may correspond to different locations within the imaged tissue throughout the sequence of images. Due to the breathing or other uncontrollable motion, evaluation of changes that occur at a particular location in an organ or other tissue over time may be erroneous.

BRIEF SUMMARY

The present invention is defined by the following claims, and nothing in this section should be taken as a limitation on those claims. By way of introduction, the preferred embodiments described below include methods and systems for morphing an ultrasound image for perfusion assessment or other purposes. Various images within a sequence of images or movie clip are mapped to one frame of reference using local warping. Nonlinear local image transformations or other warping based on local estimates of motion are used to interpolate different images to the common reference. The elastic stretching and compression of local image data results in a sequence of images where the same spatial location in each image represents the substantially same spatial location of the imaged tissue. The organ, tissue or region of interest is stationary throughout the sequence of images.

In one aspect, motion is estimated at each of a plurality of local locations between two different ultrasound images representing a same region of tissue or fluid. One ultrasound image is warped as a function of the estimated motions at the different local locations. After warping, a change as a function of time is determined for a same location based on each of the images.

In a second aspect, local estimates of motion of one or more images relative to a reference image are determined, and the images are warped as a function of the estimated motions. Each of the warped images are then displayed as a sequence of images showing the tissue as stationary as a function of time without a decrease in temporal resolution, such as caused by temporal persistence.

Further aspects and advantages of the invention are discussed below in conjunction with the preferred embodiments.

BRIEF DESCRIPTION OF SEVERAL VIEWS OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE PREFERRED EMBODIMENTS

Two or more images in a sequence are acquired representing a same tissue region, such as an organ or fluid in chamber. To counteract or account for undesired movement of the tissue relative to the transducer, local estimations of motion for one image relative to local areas of another image are determined. The local estimates of motion are used to morph the one image relative to the other image. The morphing transforms the other image so that the spatial locations or pixels of each image represent the same or substantially same tissue of the patient. Displaying the transformed images may assist in diagnosis. Where contrast agents have been injected or added to the imaged region, the change in intensity associated with any area of tissue is easily tracked as a function of time. The same spatial locations within each image represent substantially the same tissue. Perfusion assessments more accurately represent the contrast agent perfusion at the tissue location or area of interest.

Figure 1:
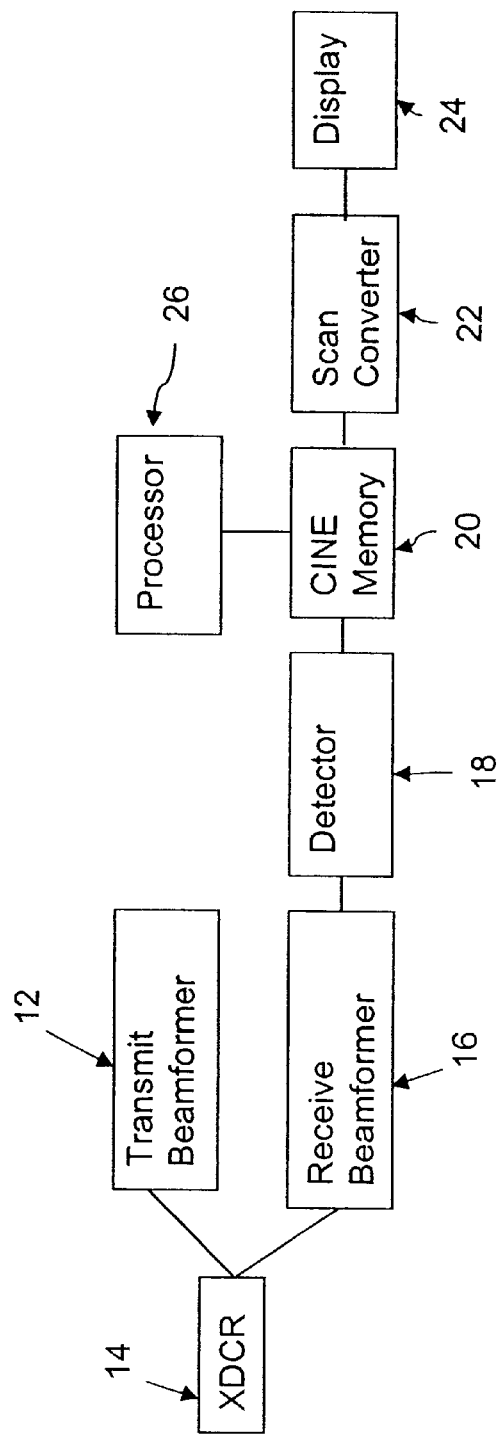
FIG. 1 is a block diagram of one embodiment of an ultrasound system for morphing ultrasound images.

FIG. 1 shows one embodiment of a system 10 for morphing an ultrasound image, such as to assist in perfusion assessment. The system 10 includes a transmit beamformer 12, a transducer 14, a receive beamformer 16, a detector or detectors 18, a CFNE memory 20, a scan converter 22, a display 24 and a processor 26. Additional, different or fewer components may be provided. For example, ultrasound images are acquired in any of various now known or later developed processes and provided to the memory 20. The memory 20, processor 26 and display 24 comprise as a workstation for morphing the ultrasound image for perfusion assessment or other purposes with or without any of the other components of the system 10.

The transmit beamformer 12 generates a plurality of electrical signals or a plane wave signal. In response, the transducer 14 generates acoustic energy focused along one or more scan lines or as a plane wave in any given transmit event. Acoustic echo signals impinge on the transducer 14. The transducer 14 generates electrical signals at each of a plurality of elements in response to the echoes. In response to the received electrical signals, the receive beamformer 16 generates data representing one or more scan lines. By repeating the transmit and receive sequences, a region of a patient is scanned, such as in a linear, sector, Vector®, curved linear or other scanned format.

By repetitively scanning the region, a sequence of images representing a same region is obtained. The transducer 14 is held in one position to repetitively scan a substantially same region. In one embodiment, substantially no movement of the transducer is provided. Since users may unintentionally move the transducer 14 during imaging, some movement of the transducer 14 relative to the region may occur. As used herein, a substantially stationary or substantially same region is used to account for unintentional movement of the transducer 14.

The detector 18 comprises one or more of a B-mode detector, a contrast agent detector, a Doppler detector, a color flow detector, or other detectors now known or later developed to detect a characteristic of received signals. In one embodiment, the detector 18 comprises both a B-mode detector and a contrast agent detector. The B-mode detector detects an intensity or an envelope magnitude or amplitude of the received signals at each spatial location within the scanned region. The contrast agent detector comprises a B-mode detector optimized to detect contrast agent as opposed to tissue and fluid, such as a B-mode detector with a filter and/or scan sequence for detecting intensities at a second harmonic or other harmonic of the fundamental transmitted frequency. In another embodiment, the contrast agent detector detects a magnitude or amplitude of a difference or loss of correlation between two or more sequentially transmitted pulses to a same or adjacent spatial locations. Since contrast agents move or are destroyed by acoustic energy, a first pulse includes response from the contrast agent and a second pulse includes a lesser, different or no response from a destroyed or moved contrast agent. The difference between the two pulses isolates contrast agent information from stationary tissue information. In this embodiment, the contrast agent detector is a Doppler detector with a clutter filter adapted for loss of correlation detection, but other contrast agent detectors may be used. Other now known or later developed contrast agent detection techniques may be used. In alternative embodiments, the tissue region is free of added contrast agents throughout an entire imaging session.

The CINE memory 20 comprises a RAM, tape, hard drive, optical storage, or other device for storing a sequence of ultrasound images. Each image represents a substantially same scanned region, such as a scanned region associated with substantially no transducer movement. As used herein, image includes frames of data at any point within the processing path, such as at the output of the receive beamformer, detectors 18, scan converter 22, or data as actually displayed as an image on the display 24. Each image within the stored sequence of images represents the region at different times. In alternative embodiments, the memory 20 is configured using other formats than a CINE format, such as a computer memory or other memory for storing JPEG, MPEG, DICOM or other image information.

The scan converter 22 comprises one or more processors or filters for converting data in a polar coordinate format as output by the receive beamformer 16 into a Cartesian coordinate format for the display 24. In alternative embodiments, the scan pattern is associated with a Cartesian coordinate format and the scan converter is optional. The scan converter 22 interpolates input data from one format into output data on a different format, such as interpolating the pixel information from data representing one, two or more adjacent spatial locations in a different format.

The display 24 comprises a CRT, LCD, flat screen, plasma screen, an LED display, printer, charting device, or other devices for generating an image or a curve as a function of time. The display 24 displays the images in sequence for subjective assessment of perfusion or other diagnosis by a user. Alternatively or additionally, the display 24 generates a curve representing intensity or other image characteristic at one or more spatial locations as a function of time. Other calculated parameters at a given time or over a range of times may be calculated and displayed by the display 24.

The processor 26 comprises one or more general processors, digital signal processors, application specific integrated circuits, analog devices, digital devices and combinations thereof. In one embodiment, the processor 26 is a personal computer, motherboard, personal computer processor, and/or personal computer video card or video processor. Through a bus or other electrical connection, the processor 26 receives the images from the CINE memory 20. In alternative embodiments, the processor 26 connects with the output of the scan converter or other component within the system 10 for receiving images. In yet other alternative embodiments, the processor 26 is included along the data path between the receive beamformer 16 and the display 24. The processor 26 operates in real-time or off-line.

The processor 26 is operable to estimate motion at each of a plurality of local locations within an image. The motion is estimated between two different ultrasound images. The processor 26 warps one or more ultrasound images as a function of the estimated motions of the different locations. The processor 26 implements the local motion estimation and image transforms discussed below for FIG. 2. The processor 26 or another processor determines a change of intensity as a function of time for a same spatial location within the warped images corresponding to a same tissue location. In one embodiment, the processor 26 is operable to estimate motion and warp one or more images as a function of one type of data, such as B-mode data, and calculate an intensity after transforming the images of a different type of data, such as detected contrast agent information. The detected contrast agent information is warped in accordance with the transforms determined using the B-mode data.

The processor 26 implements other functions in other embodiments, such as implementing graphic user interface or control functions. In one example, the processor 26 filters or provides spatial smoothing of the estimated motions or calculated transforms prior to warping or transforming an image. Low pass spatial filtering avoids overly drastic estimates of motion. The filter characteristics are determined as a function of the application or expected amount of motion.

Figure 2:
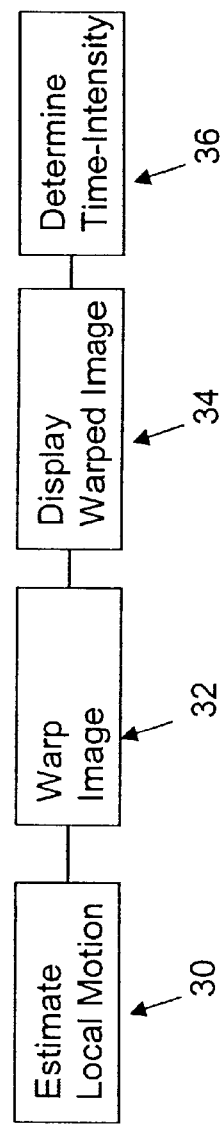
FIG. 2 is a flow chart diagram of one embodiment of a method for morphing ultrasound images.

FIG. 2 shows one embodiment of a method for morphing an ultrasound image for perfusion assessment or other purposes. Local motions of one image relative to another image are estimated in act 30. In act 32, one of the images is warped as a function the estimates of local motion. In act 34, one or more warped images are displayed, such as displaying a sequence of images warped to a common reference image. In act 36, a time-intensity curve or other parameter is calculated. In alternative embodiments, either one of act 34 and act 36 are optional or are provided independent of each other.

The sequence of images includes at least two ultrasound images representing a substantially same region without transducer movement or responsive to a substantially stationary transducer position. The region may include tissue and fluid structures that may move due to breathing, unintentional transducer movement, cyclical motion caused by the cardiac cycle, or other undesired sources of movement of the imaged tissue or the transducer 14 relative to the tissue. Any number of ultrasound images may be included in the sequence, such as 300 or more images. One of the images within the sequence or an image not within the sequence is selected as a reference image. For example, a first image within the sequence is automatically selected by the system 10. In other embodiments, other images, such as the last image or an image in the middle of the sequence, are automatically or manually selected by the system 10 or the user, respectively as a reference image. The reference image represents a common spatial frame of reference for subsequent warping or transformation of other images to the same spatial frame of reference.

In one embodiment, each of the images within the sequence of images include one type of data, such as B-mode data, Doppler data, color flow data, contrast agent data or another type of data. In other embodiments, one or more of the images, such as all of the images, include two or more types of data, such as B-mode data and contrast agent data. The different types of data are either combined and provided as a single value or are separate. For example, contrast agent and B-mode data are provided as separate sets of values. Each set of values corresponds to a same or different portion of the imaged region, such as each type of data corresponding to exclusive spatial portions of the imaged region. For any given spatial location, either a contrast agent or a B-mode value is provided. In other embodiments, a B-mode value and a contrast agent value are both provided for a same spatial location.

All of the images or a subset of the images in the sequence of images are mapped to the same reference image. The mapping is performed as a function of local warping or warping responsive to local estimates of motion. Tissue in different portions of the imaged region may move by different amounts in response to any of the sources of movement discussed herein. Motion is estimated in different local locations of one image relative to the reference image to account for the differences in movement throughout the entire image. The image is transformed or warped as a function of the local motion estimates to reposition the imaged tissue to the same position as the reference image. As a result, any spatial locations within any of the images represents a substantially same tissue location throughout the images.

In act 30, the motion at each of a plurality of local locations is estimated. The motion is estimated between two ultrasound images. For a sequence of three or more images, motion at a plurality of locations within each image of the sequence is estimated relative to a same reference image. Any of various processes now known or later developed for estimating local motion are used, such as optical flow as discussed in U.S. Pat. No. 5,503,153, the disclosure of which is incorporated herein by reference.

Figure 3:
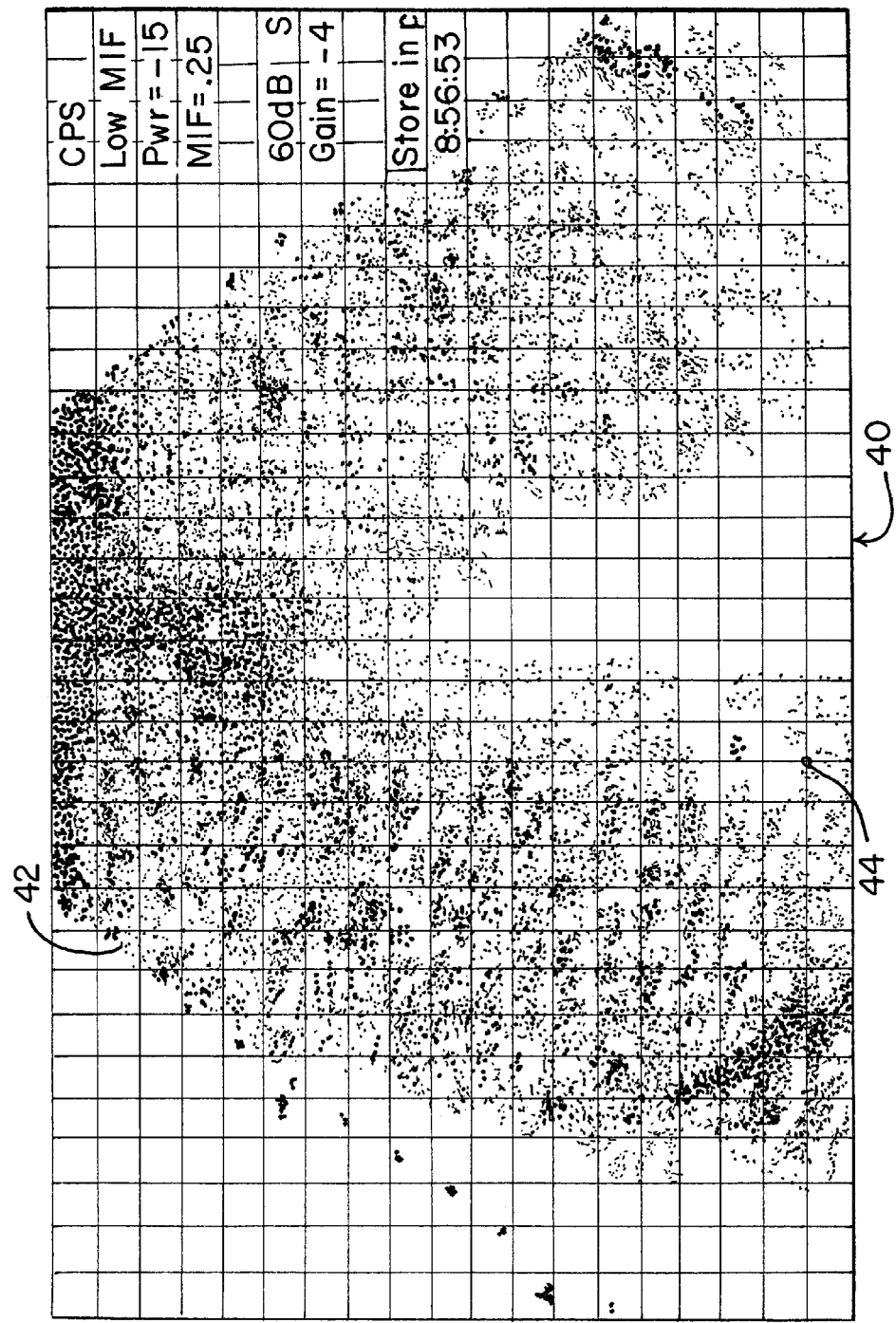
FIG. 3 is a graphical representation of one embodiment of an ultrasound image with an overlaid grid.

In one embodiment, a block matching motion analysis is used. Data representing a plurality of local areas of an image is separately correlated with data in the reference image. In one embodiment, the local estimates of motion correspond to an overlaid grid. FIG. 3 shows a grid 40 overlaid on a sector image 42. The grid 40 comprises a rectangular grid, but other grids may be used, such as triangular, polar, sector, vector, curved-vector, curvilinear, hexagonal or arbitrary grids. As shown, a grid point 44 or intersection of two grid lines is provided every 16th pixel. The grid 40 establishes a plurality of 16 pixel by 16 pixel regions. Other sized grids may be used, such as providing a grid line at every 8 pixels. The grid line spacing may vary. Each intersection of the grid lines or a grid point 44 defines a location for estimating motion. For each grid point 44, data representing an area around the grid point is correlated with data from another image, such as the reference image. The area around the grid point 44 corresponds to a same size as the grid spacing, such as a 16 by 16 pixel area surrounding the grid point, but other spacings larger than or smaller than the grid sampling size may be used.

Cross-correlations, correlation by minimizing the sum of absolute differences, maximizing the product, or other methods for correlating one data set with another data set may be used. The data for the area around each grid point 44 is compared to the data around a similar spatial location in the reference image. The data is then translated left and right and up and down in one pixel increments to identify the best correlation. The translation of the data extends along a 16 pixel range in both dimensions such that the center of the search area data is positioned at every pixel within a 16 by 16 pixel area on the reference image. Other search patterns using adaptive searching, skipping pixels, a greater or lesser range of searching or other differences may be used. For example, where the effects of the undesired motion are likely in one direction, a search pattern may be refined to search first or primarily along a direction of expected motion. A correlation threshold may indicate a proper correlation along an expected path of motion. In addition to correlation by shifting the data around each grid point using left-right and up-down directions, correlation may also be done by rotating the data around each grid point. In alternative embodiments, the motion is estimated as a function of Doppler data and direction of movement information. Other techniques now known or later developed for estimating motion at different local locations of one image with respect to another image may be used. In one embodiment, Pentium MMX/SSE2 instructions are used for determining the correlations.

In one embodiment, the local estimates of motion are filtered. For example, a low pass spatial filter filters the estimated motion vectors or magnitude of the translation of each grid point 44 relative to other grid points 44. The estimates of motions are filtered by spatially averaging over a 3×3 grouping of adjacent local estimates of motion, but unequal weightings, different spatial distributions or other spatial filtering may be provided. In alternative embodiments, no filtering is provided. In yet other alternative embodiments, an analysis or thresholding is applied to identify estimates of motion that are likely erroneous. Any erroneous estimates of motion are discarded and replaced by a further estimate of motion or by interpolating an estimate of motion from adjacent estimates of motion. Temporally or spatially adjacent estimates may be used. Temporal filtering may be used where estimated local motions are expected to vary similarly as a function of time. The estimated local motions are filtered prior to further warping of the image.

Figure 4:
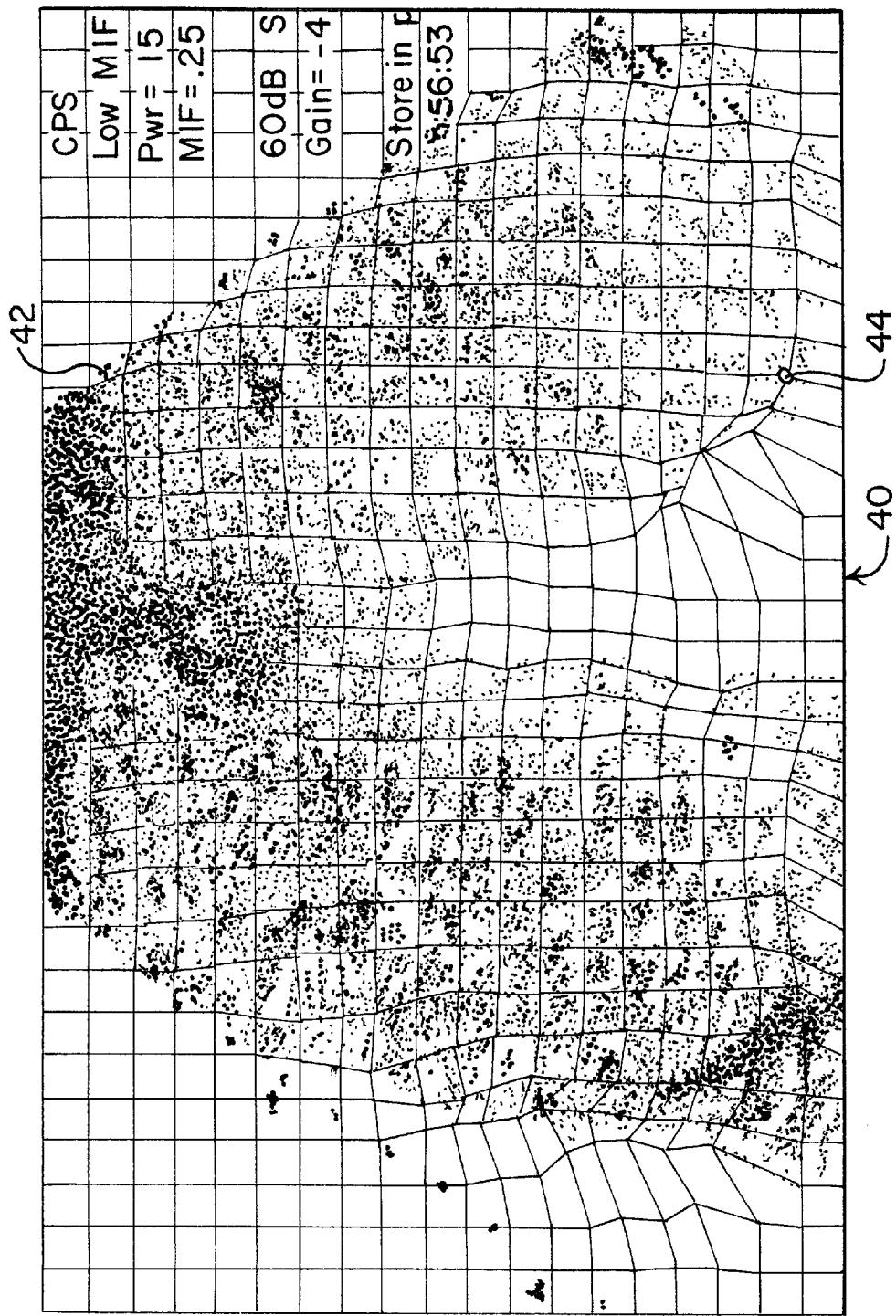
FIG. 4 is a graphical representation of another embodiment of an ultrasound image with an overlaid grid transformed as a function of local estimates of motion.

The grid 40 is warped based on the local estimates of motion. The grid points 44 are shifted as a function of the estimates of motion as shown in FIG. 4. The estimate of motion provides a motion vector or a magnitude and direction of motion corresponding to the grid point 44 within an image relative to the reference image. As shown in FIG. 4, different grid points are shifted in different directions and by different amounts, resulting in a grid 40 with a plurality of different sizes and shapes of quadrilaterals. In alternative embodiments, the shifts are limited to shifts along a single axis. Grid points 44 along the edge of the image 42 may be held stationary or shifted as a function of a changing amount of shift of adjacent but more interior grid points 44. Where the correlation is provided more inwardly within the image for an edge point, the edge grid points are shifted based on the correlation instead.

For each image of the sequence of images, the image is warped as a function of local motions estimated for the respective image in act 32. For example, the image 42 is warped as a function of the adjusted or warped grid 40 shown in FIG. 4. Warping the image data to correspond to the local estimates of motion results in images having suppressed motion relative to the reference image.

To warp the image data based on the shifted grid 40, the image data is interpolated as a function of the local estimated motions or shifted grid 40. In one embodiment, the data within a grid box prior to warping is mapped or deformed into the quadrilateral after warping the grid 40. The data is linearly interpolated to evenly space the data based on the warped grid or estimates of motion. In one embodiment, texture mapping is provided using OpenGL commands to linearly interpolate the data in two dimensions. In other embodiments, other graphical application programming interfaces, such as DirectX, Direct3D or GDI+, all by Microsoft Corporation, Redmond, Wash., or interfaces by others may be used. Nonlinear interpolation may be used. Interpolation warps the data for any given area of the image defined by the original grid 40 into the area defined by the quadrilaterals of the adjusted or shifted grid 40 of FIG. 4. The entire image is warped as a function of a plurality of separate warping interpolations performed for separate local locations or areas. Local warping results in an image with spatial locations representing the same tissue as same spatial locations of the reference image. In an alternative embodiment, the data is translated without warping, and any spatial locations or pixels corresponding to an absence of data due to a difference in local estimated motion are filled by interpolation or extrapolation.

Subsequent or other images in the sequence are warped relative to the same reference image. Each image may be warped independent of other to be or warped images. In one embodiment, each succeeding image is warped as a function of the warping of previous images. Warping in dependence on previous images simplifies estimating motion where motion may continue throughout the image sequence, resulting in a large amount of motion from the reference image to any given image within the sequence. For example, an image sequence includes three sequential ultrasound images representing substantially a same region without transducer movement. The first image in the sequence is used as a reference image. The second image in the sequence is warped as discussed above based on estimated motions in comparison with the first or reference image. For the subsequent or third image, motion is estimated at each of a plurality of local locations based on a comparison between the third image and the second image. For this comparison, the second image data corresponds to data prior to warping the second image, such as a separately saved data set representing the unwarped second image. Since the second image is unresponsive to warping, the estimates of motion at each of the grid points 44 for the third image represent motion between the second and third images regardless of the reference image. Interpolation parameters (i.e. motion vectors) are determined for the third image based on the estimates of motion between the second and third images. The interpolation parameters correspond to warping the third ultrasound image as a function of the estimated local motions from the second image. Prior to warping the third image, the interpolation parameters associated with warping the second image relative to the reference image are combined with the interpolation parameters associated with warping the third image to the second image. Where linear interpolation is provided, the interpolation parameters are summed. The summed linear interpolation parameters represent the interpolation for warping the third ultrasound image to the frame of reference of the reference image. Other combinations of interpolation parameters may be used.

Figure 5:
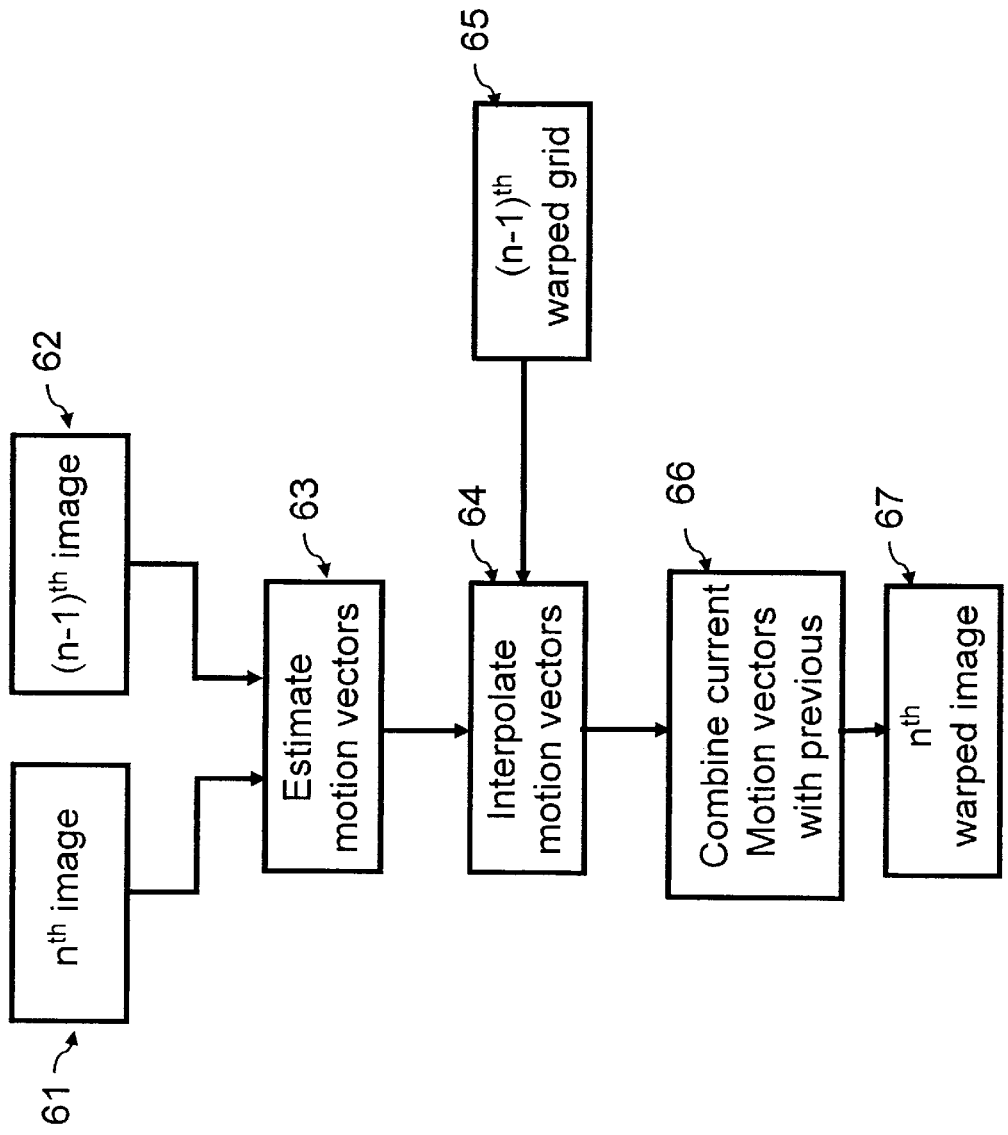
FIG. 5 is another flow chart diagram of another embodiment of a method for morphing ultrasound images.

FIG. 5 shows one further embodiment where a sequence N images are warped to a same reference. For any given n, warped and unwarped versions and the associated grids and motion vectors of each image have been determined for any previous n−1, n−2, . . . to 1 images. The nth image 61 and (n−1)th image 62 are used to estimate the motion vectors 63 for grid points from the unwarped (n−1)th image. The motion vectors for the nth image 61 are then estimated by interpolating 64 the motion vectors from the motion vectors determined for grid points in 63. The motion vectors determined for n−1, including motion vectors from images previous to n−1, are combined 66 with the motion vectors interpolated in 64. The nth image is then warped using the combined motion vectors. The above is repeated for all N images. In the end, all the images are warped to the frame of reference of the $1^{st}$ image in the sequence. The above process can be reversed if the reference frame is the last image in the sequence or performed in both a forward and backward process where the reference image is within the sequence.

Figure 6:
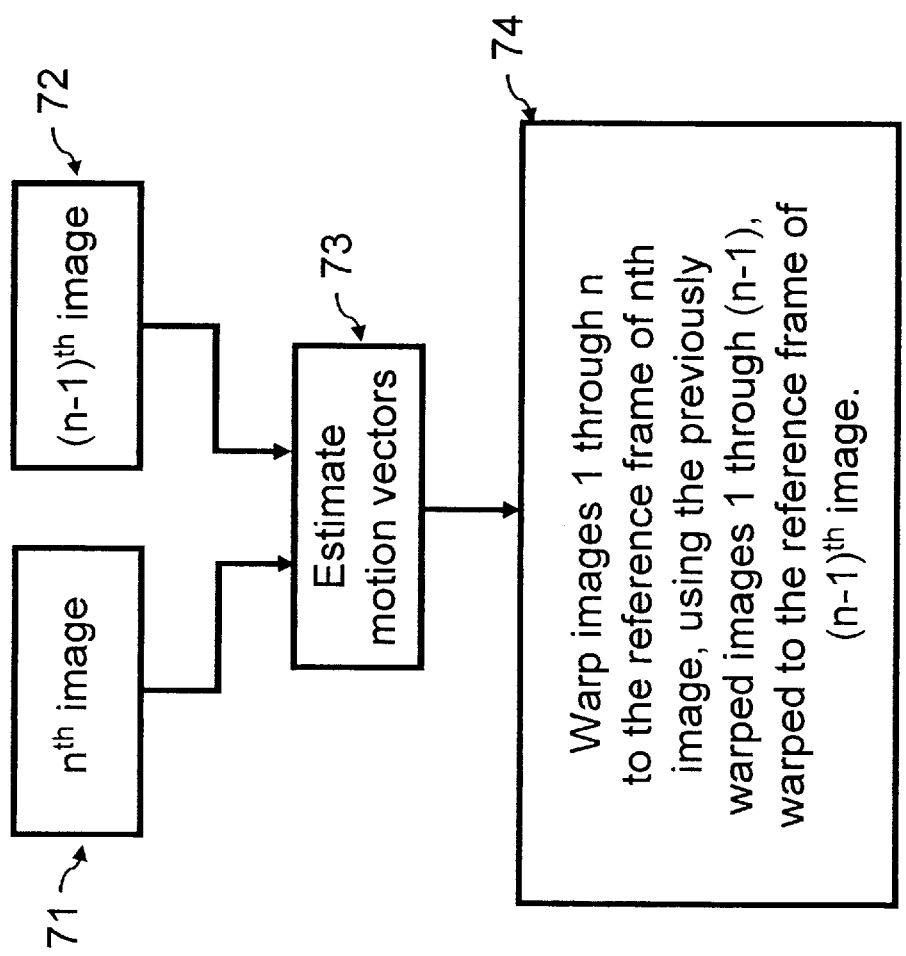
FIG. 6 is yet another a flow chart diagram of yet another embodiment of a method for morphing ultrasound images

FIG. 6 shows an alternate embodiment using repetitive or iterative warping. The nth image 71 and (n−1)th image 72 are used to first estimate the motion vectors 73 at each unwarped grid point from the (n−1)th image. Prior to this, all the images 1 through n−1 are assumed to be warped to be in the reference frame of the (n−1)th image. Using the above motion estimates for n−1 to n, all the images 1 through n are warped to be in the reference frame of the nth image. The above steps are repeated for all N. At the end, all the images are warped to the frame of reference of the last image in the sequence. The above process can be reversed if the reference frame is the first image in the sequence. Other iterative or repetitive warping may be used.

The sequence of images are B-mode images in one embodiment, but other images including different types of data or combinations of different types of data may be used. For example, the images include both B-mode data and contrast agent data. The local estimates of motion and warping are determined based on the B-mode information. The contrast agent or other information is then warped based on the interpolation parameters or warping identified using the B-mode information. By estimating motion based on the B-mode information and not on the contrast agent information, the wash-in and wash-out of contrast agent does not adversely affect the warping.

One or more warped images of the sequence are separately displayed in act 34. By sequentially and separately displaying each of the warped images, the temporal resolution is maintained for viewing any changes, such as perfusion. In one embodiment, no temporal filtering of the images within the image sequence is provided. In alternative embodiment, temporal filtering of the warped images is provided.

As an alternative or an additional act, a time-intensity curve is determined in act 36. In one embodiment, the time-intensity curve is determined using contrast agent data or data representing a spatial location associated with the perfusion of contrast agent. Other types of data may be used for any of various time-intensity or other calculations. A change as a function of time for a same spatial and associated tissue location is determined from two or more images within the sequence after warping. Since the images are warped to a common reference image, a same spatial location in each image represents a same tissue location. The intensity or other value associated with a particular spatial location or area within each of the images of the sequence is determined. Since each of the images of the sequence represent the region at different times, the graph provides a time-intensity curve. Where the intensity represents contrast agents, the time-intensity curve represents a rate of perfusion. The intensity as a function of time provides a wash-in, wash-out or combinations thereof of contrast agent. The user selects or the system automatically determines an area of interest associated with the perfusion of contrast agent, such as an area of a likely tumor in a liver, kidney or other organ. Since tumors may have increased blood flow capacity, the amount and rate of perfusion of contrast agent into the tumor is greater than for other areas of tissue. Time-intensity curves showing the wash-in and wash-out of contrast agent may be calculated for various locations within the tissue and the corresponding spatial locations within the images. A difference in wash-in and wash-out between two different spatial locations or areas may be determined and displayed. Since the time evolution of the image intensity at a particular pixel corresponds to the time evolution of contrast agent density at a particular point in the region or tissue of the patient, the time-intensity curve or change as a function of time at the spatial location across multiple images shows perfusion. Each spatial location within each image in the sequence represents a substantially same tissue, resulting in more accurate parametric images and calculations of perfusion. In one embodiment, abnormal image intensity modulations due to the stretching or compression of warping are compensated by modulating the image intensities with the Jacobian of the transformation or other filtering.

A parametric image may also be generated from the warped sequence of contrast images. In this case, each pixel of the parametric image is color-coded according to a parameter derived from the time-intensity curve associated with that pixel or spatial location. These parameters include, for example, the time of arrival, rise time, rise time modulated by the peak amplitude, and/or peak amplitude. The parametric image may be mixed with either the B-Mode image or the contrast image or both or displayed separately.

While the invention has been described above by reference to various embodiments, it should be understood that many changes and modifications can be made without departing from the scope of the invention. For example, images in a sequence are warped as a function of local estimates of motion to display images or calculate values from other types of ultrasound data, such as Doppler or B-mode data rather than contrast agent data.

It is therefore intended that the foregoing detailed description be understood as an illustration of the presently preferred embodiments of the invention, and not as a definition of the invention. It is only the following claims, including all equivalents, that are intended to define the scope of this invention.

What is claimed is:

1. A method for morphing an ultrasound image for perfusion assessment, the method comprising:
    (a) estimating motion at each of a plurality of local locations between first and second ultrasound images where the first and second ultrasound images represent a same region substantially without transducer movement;
    (b) warping the second ultrasound image as a function of the estimated motions; and
    (c) determining a change as a function of time for a same location in the first and second images after (b).

2. The method of claim 1 wherein (c) comprises determining a change in intensity at the same location as a function of time, the second ultrasound image representing the same region at a different time than the first ultrasound image.

3. The method of claim 1 wherein (c) comprises determining a rate of perfusion where the first and second ultrasound images include added contrast agent information.

4. The method of claim 1 wherein the first and second ultrasound images include B-mode and added contrast agent information, (a) and (b) comprise estimating and warping based on the B-mode information and (c) comprises determining the change based on the added contrast agent information, the added contrast agent information representing the same location responsive to (a) and (b).

5. The method of claim 1 wherein (a) comprises estimating motion at each of a plurality of grid points applied to the second ultrasound image.

6. The method of claim 5 wherein (a) comprises calculating correlations of data from the second ultrasound image representing areas around each of the grid points with data from the first ultrasound image.

7. The method of claim 5 further comprising:
    (d) warping a grid corresponding to the grid points shifted as a function of the estimated motions of (a);
    wherein (b) comprises interpolating data of the second ultrasound image as a function of the warped grid.

8. The method of claim 1 wherein (b) comprises interpolating data of the second ultrasound image as a function of the estimated motions.

9. The method of claim 1 further comprising:
    (d) warping a third ultrasound image as a function of estimated motions relative to the first ultrasound image where the third ultrasound images represent the same region substantially without transducer movement.

10. The method of claim 9 wherein (d) comprises:
    (d1) estimating motion at each of a plurality of local locations between the second ultrasound image unresponsive to (b) and the third ultrasound image;
    (d2) determining interpolation parameters corresponding to warping the third ultrasound image as a function of the estimated motions of (d1);
    (d3) combining interpolation parameters from (b) with interpolation parameters from (d2); and
    (d4) warping the third ultrasound image as a function of the combined interpolation parameters.

11. The method of claim 1 further comprising:
    (d) spatially filtering the estimated motions of (a) prior to (b).

12. A system for morphing an ultrasound image for perfusion assessment, the system comprising:
    a memory for storing first and second ultrasound images representing a same region substantially without transducer movement; and
    a processor operable to estimating motion at each of a plurality of local locations between the first and second ultrasound images, warp the second ultrasound image as a function of the estimated motions, and determine a change of intensity as a function of time for a same location in the first and second images after warping.

13. The system of claim 12 further comprising:

a B-mode detector for acquiring B-mode data of the first and second ultrasound images, the processor operable to estimate and warp as a function of the B-mode data; and a contrast agent detector for acquiring added contrast agent information of the first and second ultrasound images, the processor operable to determine the change in intensity based on the added contrast agent information, the added contrast agent information representing the same location responsive to the estimation and warping based on the B-mode data.

14. The system of claim 12 wherein the processor is operable to calculate correlations of data from the second ultrasound image representing areas around each of a plurality of grid points with data from the first ultrasound image, warp a grid corresponding to the grid points shifted as a function of the estimated motions responsive to the correlations and interpolate data of the second ultrasound image as a function of the warped grid.

15. The system of claim 12 further comprising:

a filter operable to spatially filtering the estimated motions prior to warping.

16. A method of morphing an ultrasound image for perfusion assessment, the method comprising:

(a) estimating motion at each of a plurality of locations within each of a sequence of images, the motions for each image estimated relative to a same reference image, the reference image and the images of the sequence of images corresponding to a substantially same region and a substantially stationary transducer position;

(b) warping each of the images of the sequence of images as a function of the motions estimated for the respective image; and (c) separately displaying each of the images of the sequence of images after (b).

17. The method of claim 16 wherein (a) and (b) comprise mapping all of the images in the sequence of images to the same reference image as a function of local warping.

18. The method of claim 16 wherein each of the images after (b) correspond to images having suppressed motion such that same spatial locations within each image of the sequence of images substantially represent the same tissue;

further comprising:

(d) calculating a time-intensity curve for a same spatial location from the sequence of images, each of the images of the sequence of images representing the region at different times.

19. The method of claim 18 wherein (d) comprises calculating one of a wash-in curve, wash-out curve and combination thereof where the sequence images include information responsive to added contrast agents in the region.

20. The method of claim 16 wherein (a) comprises separately correlating data representing a plurality of local areas of each of the images of the sequence of images to the reference image and (b) comprises interpolating data of each of the images of the sequence of images as a function of the correlations of (a).

21. The method of claim 1 wherein (c) comprises deriving a parameter image as a function of the change at a plurality of spatial locations.

22. The method of claim 1 further comprising:

(d) repetitively warping the second ultrasound image as a function of motion vectors related to other ultrasound images.

* * * * *